United States Patent
Hirakawa et al.

(10) Patent No.: US 11,574,717 B2
(45) Date of Patent: Feb. 7, 2023

(54) MEDICAL DOCUMENT CREATION SUPPORT APPARATUS, MEDICAL DOCUMENT CREATION SUPPORT METHOD, AND MEDICAL DOCUMENT CREATION SUPPORT PROGRAM

(71) Applicant: FUJIFILM Corporation, Tokyo (JP)

(72) Inventors: Shinnosuke Hirakawa, Tokyo (JP); Keigo Nakamura, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 78 days.

(21) Appl. No.: 17/037,600

(22) Filed: Sep. 29, 2020

(65) Prior Publication Data

US 2021/0027872 A1    Jan. 28, 2021

Related U.S. Application Data

(63) Continuation of application No. PCT/JP2019/011878, filed on Mar. 20, 2019.

(30) Foreign Application Priority Data

Apr. 4, 2018    (JP) .............................. JP2018-072523

(51) Int. Cl.
  *G16H 15/00*    (2018.01)
  *G16H 30/20*    (2018.01)
  *G16H 30/40*    (2018.01)

(52) U.S. Cl.
  CPC ............. *G16H 15/00* (2018.01); *G16H 30/20* (2018.01); *G16H 30/40* (2018.01)

(58) Field of Classification Search
  CPC .............................. G16H 30/20; G16H 30/40
  See application file for complete search history.

(56) References Cited

U.S. PATENT DOCUMENTS

| | | | |
|---|---|---|---|
| 10,853,526 B2* | 12/2020 | Li | .......................... G06F 21/82 |
| 2008/0002911 A1* | 1/2008 | Eisen | ................. H04N 1/00872 382/283 |
| 2009/0076853 A1 | 3/2009 | Sagawa | |
| 2009/0228303 A1* | 9/2009 | Faulkner | ................ G16H 10/60 705/2 |

(Continued)

FOREIGN PATENT DOCUMENTS

| | | |
|---|---|---|
| JP | 2009060945 | 3/2009 |
| JP | 2009070201 | 4/2009 |

(Continued)

OTHER PUBLICATIONS

"International Search Report (Form PCT/ISA/210) of PCT/JP2019/011878," dated Jun. 18, 2019, with English translation thereof, pp. 1-5.

(Continued)

*Primary Examiner* — Robert A Sorey
(74) *Attorney, Agent, or Firm* — JCIPRNET

(57) ABSTRACT

The medical document creation support apparatus includes a visible information reception unit that receives visible information included in a current medical document, and a processing unit performs processing of suppressing a part of a content indicated by the visible information received by the visible information reception unit on the basis of at least one of a past image, a past medical document, or a predetermined rule.

15 Claims, 10 Drawing Sheets

(56) References Cited

U.S. PATENT DOCUMENTS

| | | | |
|---|---|---|---|
| 2010/0256459 A1 | 10/2010 | Miyasa et al. | |
| 2012/0304304 A1* | 11/2012 | Avrahami | H04L 9/085 726/27 |
| 2013/0325497 A1 | 12/2013 | Kanada | |
| 2014/0047234 A1* | 2/2014 | Davis | G06Q 10/10 713/160 |
| 2015/0143540 A1* | 5/2015 | Shelton | G06F 21/6218 726/28 |
| 2015/0310177 A1* | 10/2015 | Csurka | G06N 5/02 706/50 |
| 2016/0299144 A1* | 10/2016 | Blume | G01N 33/57419 |
| 2017/0132186 A1* | 5/2017 | Plummer | G09C 1/00 |
| 2018/0336972 A1* | 11/2018 | Carbonell | G16H 40/20 |
| 2019/0213336 A1* | 7/2019 | Kundu | G06F 16/683 |
| 2020/0097713 A1* | 3/2020 | Cramer | G06V 30/414 |

FOREIGN PATENT DOCUMENTS

| | | |
|---|---|---|
| JP | 2009082441 | 4/2009 |
| JP | 2009238038 | 10/2009 |
| JP | 2011002997 | 1/2011 |
| JP | 2013171526 | 9/2013 |
| JP | 2013252160 | 12/2013 |
| JP | 2016040688 | 3/2016 |

OTHER PUBLICATIONS

"Written Opinion of the International Searching Authority (Form PCT/ISA/237) of PCT/JP2019/011878," dated Jun. 18, 2019, with English translation thereof, pp. 1-17.

"Office Action of Japan Counterpart Application" with English translation thereof, dated Dec. 14, 2021, p. 1-p. 11.

* cited by examiner

```
                                        36
┌─────────────────────────┐
│ MARCH 15, 2018          │
├─────────────────────────┤
│ FINDINGS                │
│                         │
│ NODULE HAVING CIRCULAR  │
│ SHAPE OF 23 × 19 mm IS  │
│ RECOGNIZED IN LOWER     │
│ LOBE S6b OF RIGHT LUNG. │
│                         │
└─────────────────────────┘
```

FIG. 9

```
                                        36
┌─────────────────────────┐
│ MARCH 15, 2018          │
├─────────────────────────┤
│ FINDINGS                │
│                         │
│ NODULE IN LOWER LOBE    │
│ S6b OF RIGHT LUNG.      │
│                         │
└─────────────────────────┘
```

FIG. 10
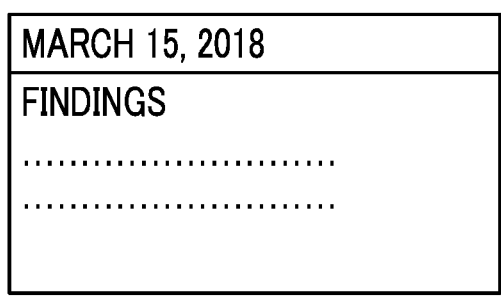
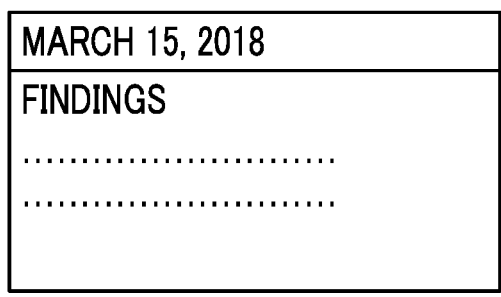
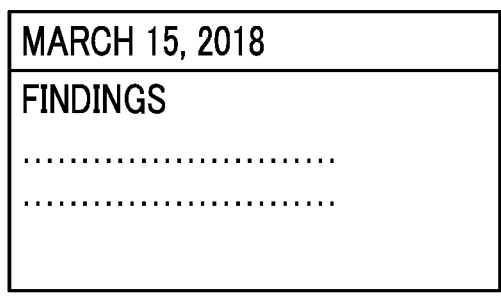
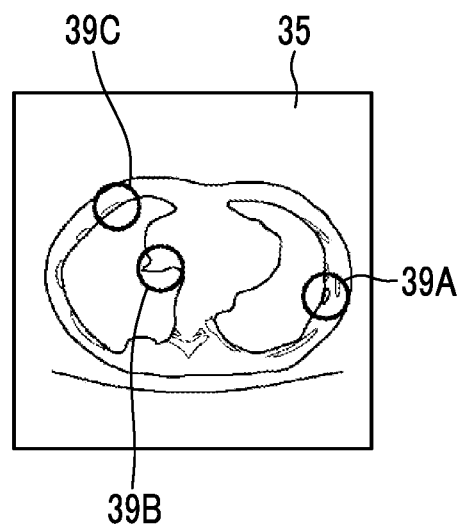

MEDICAL DOCUMENT CREATION SUPPORT APPARATUS, MEDICAL DOCUMENT CREATION SUPPORT METHOD, AND MEDICAL DOCUMENT CREATION SUPPORT PROGRAM

CROSS-REFERENCE TO RELATED APPLICATION

The present application is a continuation application of International Application No. PCT/JP2019/011878, filed Mar. 20, 2019, which claims priority to Japanese Patent Application No. 2018-072523, filed Apr. 4, 2018. The contents of these applications are incorporated herein by reference in their entirety.

BACKGROUND

Field of the Invention

The present invention relates to a medical document creation support apparatus, a medical document creation support method, and a medical document creation support program.

Related Art

In recent years, advances in medical apparatuses, such as computed tomography (CT) apparatuses and magnetic resonance imaging (MRI) devices, have enabled image diagnosis using high-resolution three-dimensional medical images with higher quality. In particular, since a region of a lesion can be accurately specified by image diagnosis using CT images, MRI images, and the like, appropriate treatment can be performed based on the specified result.

A medical image is analyzed by computer-aided diagnosis (CAD) using a discriminator learned by deep learning or the like, regions, positions, volumes, and the like of lesions included in the medical image are extracted, and these are acquired as the analysis result. The analysis result generated by an analysis process in this manner is stored in a database so as to be associated with examination information, such as a patient name, gender, age, and a modality that has acquired the medical image, and provided for diagnosis. At this time, a radiology technician who acquired medical images determines a radiologist according to the medical image and informs the determined radiologist that the medical image and the CAD analysis result are present. The radiologist interprets the medical image with reference to the transmitted medical image and analysis result and creates an interpretation report in his or her own interpretation terminal apparatus.

Various methods have been proposed for referring to a finding sentence and the like described in a past interpretation report (hereinafter referred to as a past report) at the time of creating a current interpretation report (hereinafter referred to as a current report). For example, JP2009-070201A discloses a method for simply creating the interpretation report by copying comments described in the past report, creating information related to a current image from information related to a past image, and creating a template for creating the current report.

On the other hand, in medical documents such as the interpretation report, it is desired that necessary matters are described concisely to enable a diagnostician and a radiologist who read medical documents to easily and quickly grasp contents described in the medical documents. However, in an interpretation report creation apparatus disclosed in the above-described JP2009-070201A, a template created by copying comments described in the past report as they are is used for creating the current report. Therefore, even in a case where a comment is necessary in the past report, an unnecessary comment may be used in the template in the current report. In this case, in a case where a diagnostician and a radiologist read the current report, it may be difficult to grasp contents of the necessary comment easily and quickly.

In addition, even in a case where a method of describing comments in the current report is different from the preference of the diagnostician who reads the current report, or in a case where a method of describing comments differs depending on the current report, it may be difficult to grasp contents which are described in the current report.

SUMMARY

The present invention has been made in view of the above circumstances, and an object of the present invention is to make it possible to easily and quickly grasp contents necessary for diagnosis in the medical document.

The medical document creation support apparatus according to the embodiment of the present invention comprises a visible information reception unit that receives visible information included in a current medical document, and a processing unit performs processing of suppressing a part of a content indicated by the visible information received by the visible information reception unit on the basis of at least one of a past image, a past medical document, or a predetermined rule.

In addition, in the medical document creation support apparatus according to the embodiment of the present invention, the processing unit may perform processing of setting a display or a non-display for each item indicated by the visible information in the current medical document.

In addition, in the medical document creation support apparatus according to the embodiment of the present invention, the visible information is character information, and the processing unit may perform processing of setting a display or a non-display for each character string indicated by the character information in the current medical document.

In addition, in the medical document creation support apparatus according to the embodiment of the present invention, in a case where there are a plurality of items indicated by the visible information, the processing unit may perform processing of combining contents indicated by two or more items in the current medical document.

In addition, in the medical document creation support apparatus according to the embodiment of the present invention, the processing unit may perform processing of restoring a content indicated by the suppressed visible information.

In addition, in the medical document creation support apparatus according to the embodiment of the present invention, the processing unit may perform processing of suppressing the content indicated by the visible information in a stepwise manner.

In addition, in the medical document creation support apparatus according to the embodiment of the present invention, the processing unit may perform processing of restoring the content indicated by the suppressed visible information in a stepwise manner.

In addition, in the medical document creation support apparatus according to the embodiment of the present invention, the past image and the past medical document may be information targeting a subject different from a subject who is a target of the current medical document.

In addition, in the medical document creation support apparatus according to the embodiment of the present invention, the current medical document may be a document based on a current image obtained by imaging a subject.

In addition, in the medical document creation support apparatus according to the embodiment of the present invention, the visible information reception unit may receive visible information based on a current medical document created on the basis of an image analysis result of a position designated on the current image.

In addition, in the medical document creation support apparatus according to the embodiment of the present invention, the visible information reception unit may receive visible information based on a current medical document created on the basis of an image analysis result of the entire current image.

In addition, in the medical document creation support apparatus according to the embodiment of the present invention, the visible information reception unit may receive visible information based on a current medical document created on the basis of a past image or a past medical document acquired in the past for a subject in the current image.

In addition, in the medical document creation support apparatus according to the embodiment of the present invention, the visible information reception unit may receive visible information based on a current medical document created by at least one of a radiologist or a diagnostician on the basis of the current image.

A medical document creation support method according to the embodiment of the present invention includes receiving visible information included in a current medical document based on a current image acquired by imaging a subject, and performing processing of suppressing a content indicated by the received visible information on the basis of at least one of a past image, a past medical document, or a predetermined rule.

A medical document creation support program according to the embodiment of the present invention causes a computer to execute a procedure for receiving visible information included in a current medical document based on a current image acquired by imaging a subject, and a procedure for performing processing of suppressing a content indicated by the received visible information on the basis of at least one of a past image, a past medical document, or a predetermined rule.

Another medical document creation support apparatus according to the embodiment of the present invention comprises a memory that stores instructions to be executed by a computer, and a processor that is configured to execute the stored instructions, in which the processor executes processing of receiving visible information included in a current medical document based on a current image acquired by imaging a subject, and suppressing a content indicated by the received visible information on the basis of at least one of a past image, a past medical document, or a predetermined rule.

In the present invention, processing of suppressing the content indicated by the visible information included in the current medical document is performed on the basis of at least one of a past image, a past medical document, or a predetermined rule. Therefore, the contents unnecessary for diagnosis are suppressed in the current medical document, so that a diagnostician and a radiologist can easily and quickly grasp the contents necessary for diagnosis described in the medical document.

BRIEF DESCRIPTION OF THE DRAWINGS

FIG. 3 is a diagram showing an interpretation report screen.

FIG. 8 is a diagram for explaining a display in which a content of findings is suppressed in a stepwise manner.

FIG. 9 is another diagram for explaining a display in which a content of findings is suppressed in a stepwise manner.

FIG. 10 is a diagram for explaining a display in a case where there are a plurality of items.

DETAILED DESCRIPTION

Figure 1:
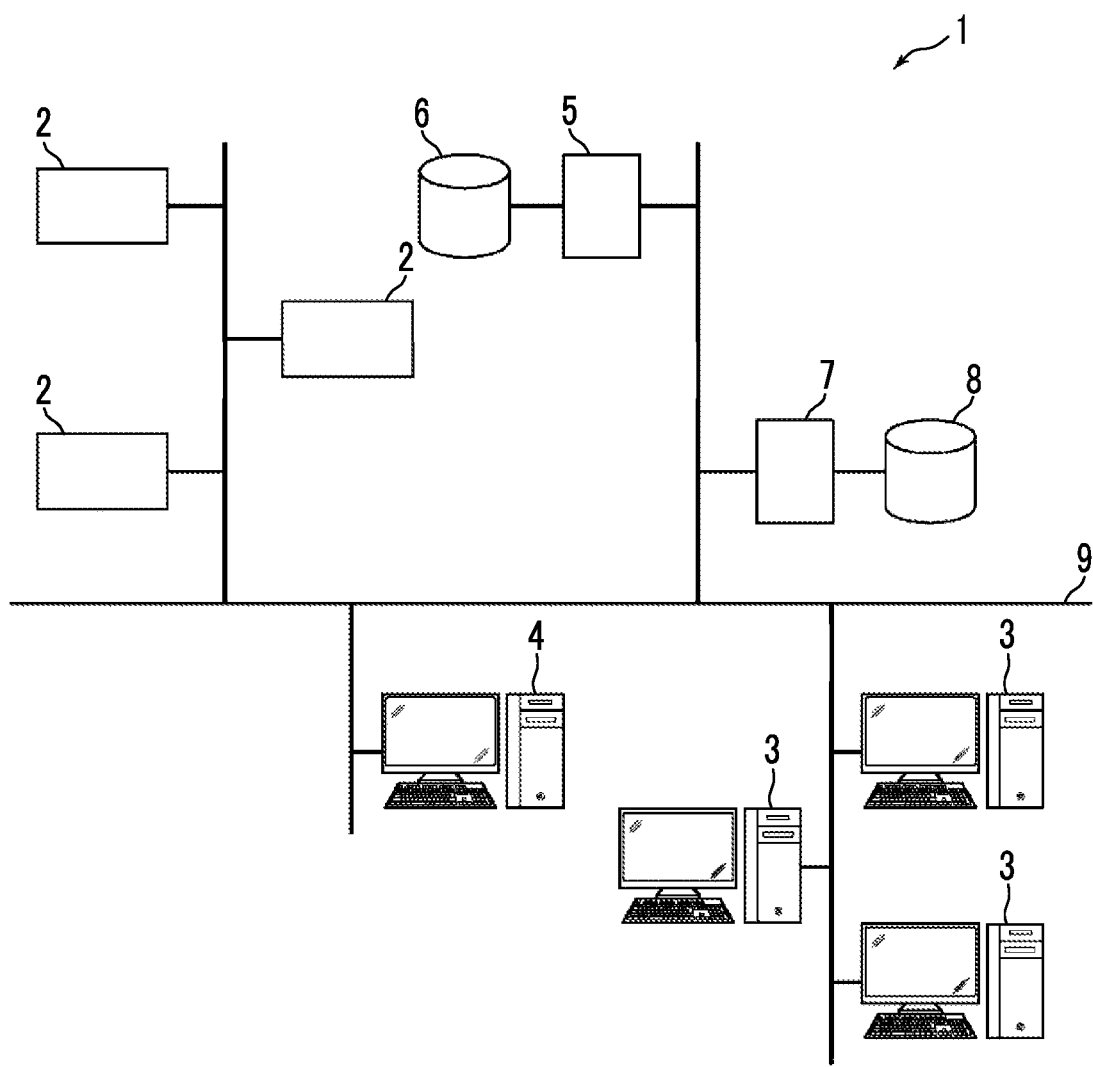
FIG. 1 is a diagram showing a schematic configuration of a medical information system to which a medical document creation support apparatus according to an embodiment of the invention is applied.

Hereinafter, an embodiment of the invention will be described with reference to the accompanying diagrams. FIG. 1 is a diagram showing a schematic configuration of a medical information system to which a medical document creation support apparatus according to the first embodiment of the invention is applied. A medical information system 1 shown in FIG. 1 is a system for performing imaging of an examination target part of a subject, storage of a medical image acquired by imaging, interpretation of a medical image by a radiologist and creation of an interpretation report, and viewing of an interpretation report by a diagnostician in a medical department of a request source and detailed observation of a medical image to be interpreted, on the basis of an examination order from a diagnostician (doctor) in a medical department using a known ordering system. As shown in FIG. 1, the medical information system 1 is configured to include a plurality of modalities (imaging apparatuses) 2, a plurality of interpretation workstations (WS) 3 that are interpretation terminals, a medical department workstation (WS) 4, an image server 5, an image database 6, an interpretation report server 7, and an interpretation report database 8 that are communicably connected to each other through a wired or wireless network 9.

Each device is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed onto the computer from the recording medium. Alternatively, the application program is stored in a storage apparatus of a server computer connected to the network 9 or in a network storage so as to be accessible from the outside, and is downloaded and installed onto the computer as necessary.

A modality 2 is an apparatus that generates a medical image showing a diagnosis target part by imaging the diagnosis target part of the subject. Specifically, the modality 2 is a simple X-ray imaging apparatus, a CT apparatus, an MRI apparatus, a positron emission tomography (PET) apparatus, and the like. A medical image generated by the modality 2 is transmitted to the image server 5 and stored therein.

An interpretation WS 3 includes the medical document creation support apparatus according to the first embodiment. The configuration of the interpretation WS 3 will be described later.

A medical department WS 4 is a computer used by a diagnostician in a medical department to observe the details of an image, view an interpretation report, create an electronic medical record, and the like, and is configured to include a processing apparatus, a display apparatus such as a display, and an input apparatus such as a keyboard and a mouse. In the medical department WS 4, each processing, such as the creation of a medical record of patient (electronic medical record), sending a request to view an image to the image server 5, display of an image received from the image server 5, automatic detection or highlighting of a lesion-like portion in an image, sending a request to view an interpretation report to the interpretation report server 7, and display of an interpretation report received from the interpretation report server 7, is performed by executing a software program for each process.

The image server 5 is obtained by installing a software program for providing a function of a database management system (DBMS) on a general-purpose computer. The image server 5 comprises a storage for an image database 6. This storage may be a hard disk apparatus connected to the image server 5 by a data bus, or may be a disk apparatus connected to a storage area network (SAN) or a network attached storage (NAS) connected to the network 9. In a case where the image server 5 receives a request to register a medical image from the modality 2, the image server 5 registers the medical image in the image database 6 in a format for a database.

Image data of the medical images acquired by the modality 2 or a medical image group including a plurality of medical images and accessory information are registered in the image database 6. The accessory information includes, for example, an image ID for identifying each medical image or a medical image group (hereinafter, may be simply referred to as a medical image), a patient identification (ID) for identifying a subject, an examination ID for identifying an examination, a unique ID (UID: unique identification) allocated for each medical image, examination date and examination time at which the medical image or the medical image group is generated, the type of a modality used in an examination for acquiring a medical image, patient information such as the name, age, and gender of patient, an examination part (imaging part), imaging information (an imaging protocol, an imaging sequence, an imaging method, imaging conditions, the use of a contrast medium, and the like), and information such as a series number or a collection number in a case where a plurality of medical images are acquired in one examination.

In a case where a viewing request from the interpretation WS 3 is received through the network 9, the image server 5 searches for a medical image registered in the image database 6 and transmits the searched medical image to the interpretation WS 3 that is a request source.

The interpretation report server 7 has a software program for providing a function of a database management system to a general-purpose computer. In a case where the interpretation report server 7 receives a request to register an interpretation report from the interpretation WS 3, the interpretation report server 7 registers the interpretation report in the interpretation report database 8 in a format for a database. In a case where a request to search for an interpretation report is received, the interpretation report is searched for from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, and findings, is recorded.

The network 9 is a wired or wireless local area network that connects various devices in a hospital to each other. In a case where the interpretation WS 3 is installed in another hospital or clinic, the network 9 may be configured to connect local area networks of respective hospitals through the internet or a dedicated circuit. In any case, it is preferable that the network 9 is configured to be able to realize high-speed transmission of medical images, such as an optical network.

Hereinafter, the interpretation WS 3 according to the first embodiment will be described in detail. The interpretation WS 3 is a computer used by a radiologist of a medical image to interpret the medical image and create the interpretation report, and is configured to include a processing apparatus, a display apparatus such as a display, and an input apparatus such as a keyboard and a mouse. In the interpretation WS 3, each process, such as making a request to view a medical image to the image server 5, various kinds of image processing on a medical image received from the image server 5, display of a medical image, an analysis process on a medical image, highlighting of a medical image based on the analysis result, creation of an interpretation report based on the analysis result, support for the creation of an interpretation report, making a request to register an interpretation report and a request to view an interpretation report to the interpretation report server 7, and display of an interpretation report received from the interpretation report server 7, is performed by executing a software program for each process. It should be noted that since processing other than processing performed by the medical document creation support apparatus of the first embodiment, among these processes, are performed by a known software program, the detailed description thereof will be omitted herein. In addition, the processing other than the processing performed by the medical document creation support apparatus of the first embodiment may not be performed in the interpretation WS 3, and a computer that performs the processes may be separately connected to the network 9, and requested processing on the computer may be performed according to a processing request from the interpretation WS 3.

The interpretation WS 3 includes the medical document creation support apparatus according to the first embodiment. Therefore, a medical document creation support program according to the first embodiment is installed on the interpretation WS 3. The medical document creation support program is recorded on a recording medium, such as a DVD or a CD-ROM, and distributed, and is installed onto the interpretation WS 3 from the recording medium. Alternatively, the medical document creation support program is stored in a storage apparatus of a server computer connected to the network or in a network storage so as to be accessible from the outside, and is downloaded and installed onto the interpretation WS 3 as necessary.

Figure 2:
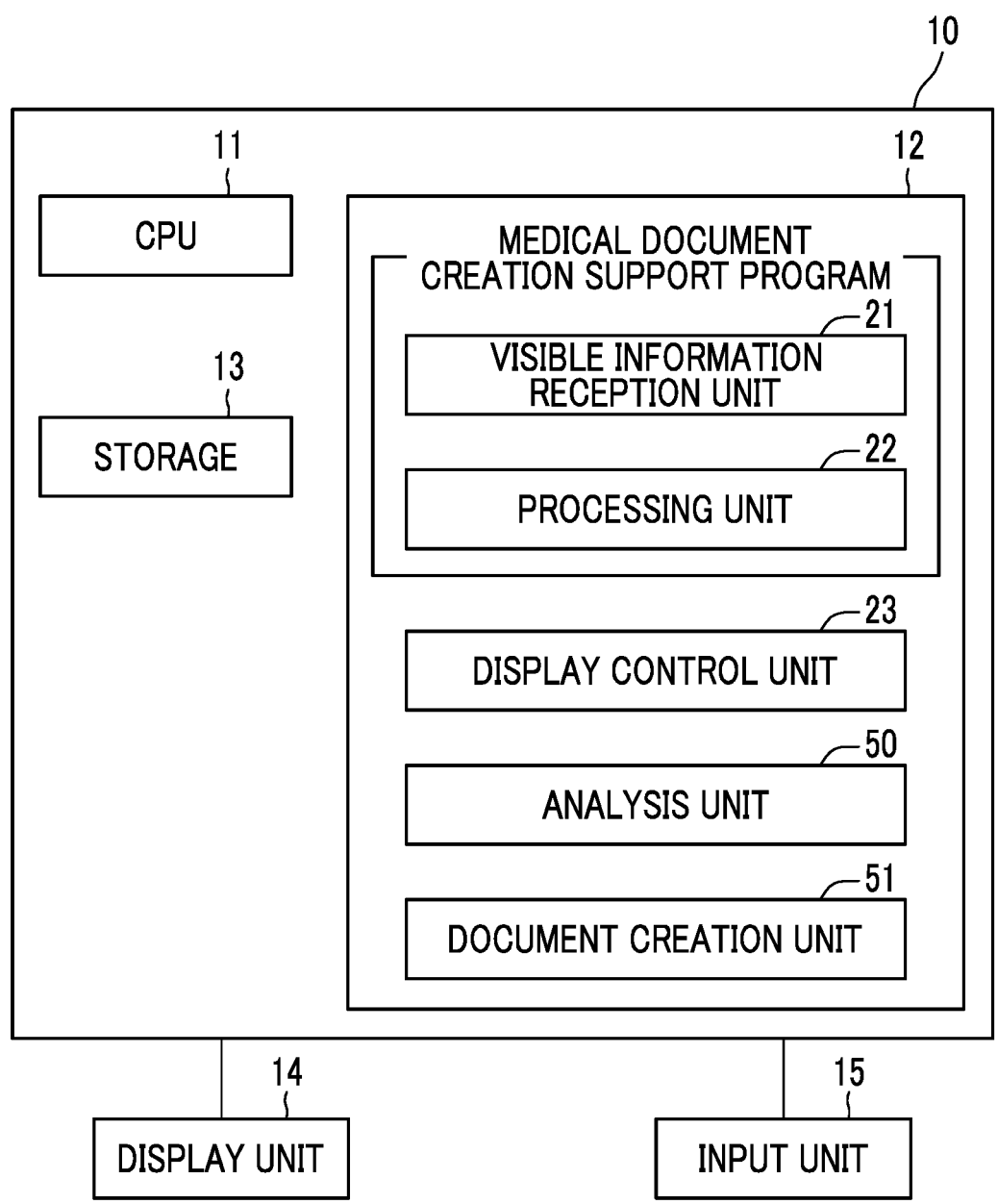
FIG. 2 is a diagram showing a schematic configuration of a medical document creation support apparatus according to the first embodiment of the present invention.

FIG. 2 is a diagram showing the schematic configuration of a medical document creation support apparatus 10 according to the first embodiment of the present invention that is realized by installing the medical document creation support program. As shown in FIG. 2, the medical document creation support apparatus 10 comprises a central processing unit (CPU) 11, a memory 12, and a storage 13 as the configuration of a standard computer. A display apparatus (hereinafter, referred to as a display unit) 14, such as a liquid crystal display, and an input apparatus (hereinafter, referred to as an input unit) 15, such as a keyboard and a mouse, are connected to the medical document creation support apparatus 10.

The storage 13 consists of a storage device, such as a hard disk or a solid state drive (SSD). Medical images and various kinds of information including information necessary for processing of the medical document creation support apparatus 10, which are acquired from the image server 5 through the network 9, are stored in the storage 13.

The medical document creation support program is stored in the memory 12. The medical document creation support program specifies, as processing to be executed by a CPU 11, visible information reception processing that receives visible information included in a current medical document, and processing of suppressing a part of a content indicated by the received visible information on the basis of at least one of a past image, a past medical document, or a predetermined rule.

In a case where the CPU 11 executes the processing in accordance with the medical document creation support program, the computer functions as a visible information reception unit 21 and a processing unit 22. It should be noted that in the first embodiment, the CPU 11 executes the function of each unit according to the medical document creation support program. However, as a general-purpose processor that executes software to function as various processing units, a programmable logic device (PLD) that is a processor whose circuit configuration can be changed after manufacturing, such as a field programmable gate array (FPGA), can be used in addition to the CPU 11. Alternatively, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. In this way, various processing units are formed using one or more of the above-mentioned various processors as hardware structures.

More specifically, the hardware structure of these various processors is an electrical circuit (circuitry) in the form of a combination of circuit elements, such as semiconductor elements.

It should be noted that in a case where the interpretation WS 3 functions as an apparatus other than the medical document creation support apparatus 10 for performing processing, the memory 12 stores a program that executes the function. For example, in the first embodiment, an analysis program is stored in the memory 12 since the interpretation WS 3 performs the analysis process. Therefore, in the first embodiment, the computer configuring the interpretation WS 3 also functions as an analysis unit 50 that executes the analysis process. In addition, in the first embodiment, a document creation program is stored in the memory 12 since the interpretation WS 3 performs medical document creation processing. Therefore, in the first embodiment, the computer configuring the interpretation WS 3 also functions as a document creation unit 51 that executes the document creation processing.

The analysis unit 50 comprises a discriminator that is machine-learned to discriminate whether or not each pixel (voxel) in the medical image represents a lesion, and the type of lesion. In the first embodiment, the discriminator consists of a neural network deep-learned such that a plurality of types of lesions included in the medical image can be classified. In a case where the medical image is input, the discriminator in the analysis unit 50 performs learning so as to output the probability of each of a plurality of lesions to each pixel (voxel) in the medical image. Then, the discriminator obtains a lesion exceeding a predetermined threshold value and having the maximum probability for a certain pixel, and discriminates that the pixel is the pixel of the determined lesion.

It should be noted that the discriminator may include, for example, a support vector machine (SVM), a convolutional neural network (CNN), or a recurrent neural network (RNN) in addition to the neural network deep-learned.

In addition, the analysis unit 50 uses a discrimination result by the discriminator to specify a type of lesion, a position of the lesion, and a size of the lesion to generate an analysis result. For example, in a case where the medical image includes a thoracoabdominal part of the human body and a lesion is found in the thoracoabdominal part, the analysis unit 50 generates an analysis result including a type, a position, and a size of the lesion in the thoracoabdominal part. More specifically, the analysis unit 50 generates character information such as "right lung", "lower lobe", "position S6b", "23×19 mm", and "nodule" as the analysis result.

In a case of creating a medical document for a medical image, the document creation unit 51 creates a medical document by inputting character information representing finding content for the medical image. In the first embodiment, the document creation unit 51 creates the medical document on the basis of the analysis result obtained by analyzing the current image acquired by imaging the subject by the analysis unit 50 and character information input from an input unit 15 to be described later. It should be noted that in the first embodiment, an interpretation report is created as the medical document. However, in the present invention, the medical document is not limited to an interpretation report, but includes documents such as a diagnosis report and an electronic medical record, and includes medical documents including (For example, an image) other than character information.

Here, in the present embodiment, the "current image" is an image to be referred to at the time of creating an interpretation report, and a plurality of tomographic images forming a three-dimensional image correspond to the current image. In the first embodiment, it is assumed that a three-dimensional image is a CT image of a thoracoabdominal part. Specifically, the interpretation WS 3 gives an instruction to the image server 5 to request a CT image that is a target of an interpretation report to be created by the radiologist this time. It should be noted that an interpretation report to be created this time (hereinafter, may be referred to as a current report) corresponds to the current medical document of the present invention. In addition, a "past image" is an image acquired before the current image is acquired. A "past medical document" is a medical document created before the current medical document is created, that is, already created. The interpretation report created in the past (hereinafter, may be referred to as a past report) corresponds to the past medical document of the present invention.

In a case where a viewing request from the interpretation WS 3 is received through the network 9, the image server 5 searches for a medical image registered in the image database 6 and transmits the searched medical image, that is, a CT image, to the interpretation WS 3 that is a request source. The interpretation WS 3 receives the CT image transmitted from the image server 5. It should be noted that the CT image received by the interpretation WS 3 is stored in the storage 13. In response to an instruction from the document creation unit 51 to be described later, the analysis unit 50 acquires the current image that is a target of the interpretation report to be created this time by searching the storage 13, and analyzes the acquired current image.

The document creation unit 51 has been learned to convert character information into sentences, and creates sentences from input character information. Specifically, the character information of "right lung", "lower lobe", "position S6b", "23×19 mm", and "nodule" included in the analysis result by the analysis unit 50 is input to the document creation unit 51. The document creation unit 51 creates an interpretation report of "a nodule of 23×19 mm is recognized in the lower lobe position S6b of the right lung." on the basis of the input character information.

In addition, the document creation unit 51 also creates an interpretation report on the basis of the character information input from the input unit 15 to be described later. Here, the document creation unit 51 has a document creating function such as converting an input character into a Chinese character, and creates a document on the basis of an input from the input unit 15 by an operator. It should be noted that the document creation unit 51 creates a document by converting voice into characters in a case where input is made by the voice.

Figure 3:
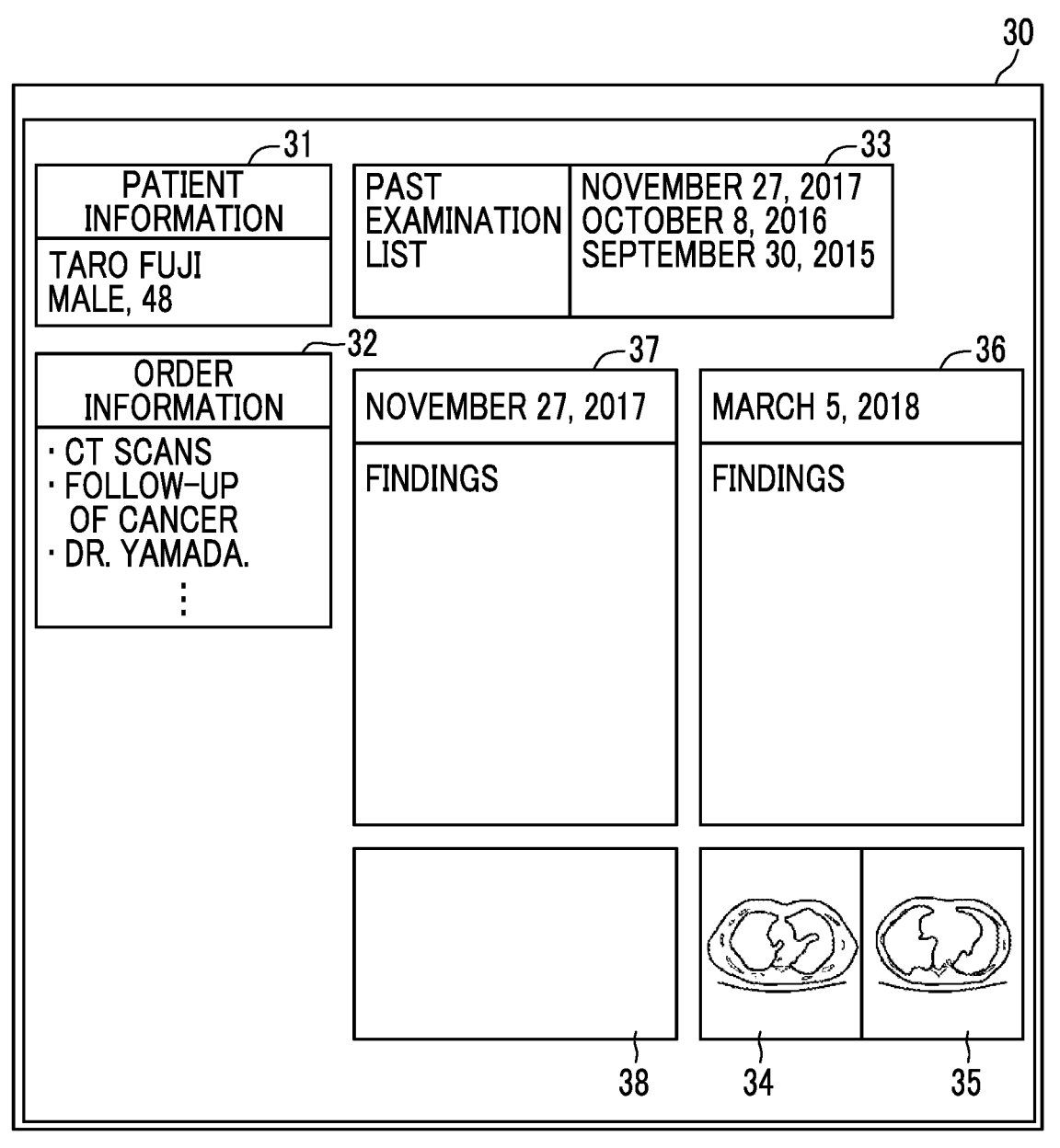

FIG. 3 is a diagram showing an interpretation report creation screen 30 displayed on a display unit 14. As shown in FIG. 3, the interpretation report creation screen 30 includes a patient information region 31 for displaying patient information indicating the name, gender, and the like of a patient to be imaged to acquire a CT image, an order information region 32 for displaying information of an examination order for a request for an examination for acquiring a CT image, an examination list region 33 for displaying a past examination list for a patient whose CT image is acquired, current images 34 and 35 to be interpreted, a creation region 36 for inputting a document for creating an interpretation report, a past interpretation report region 37 for displaying a past interpretation report including character information, and a past image region 38 for displaying a past medical image for which the interpretation report displayed in the past interpretation report region 37 was created. The radiologist (operator) who interprets the current images 34 and 35 inputs the sentence of the findings in the creation region 36 using the input unit 15.

In the first embodiment, as described above, the character information created by the document creation unit 51 on the basis of the analysis result by the analysis unit 50, that is, "a nodule of 23×19 mm is recognized in the lower lobe position S6b of the right lung." is displayed in a creation region 36 by a display control unit 23 to be described later (refer to FIG. 6). It is assumed that an operator who has viewed the creation region 36 inputs the findings that are not sufficient in the interpretation report created by the document creation unit 51 as a result of the interpretation of the current images 34 and 35. For example, it is assumed that the operator inputs character information such as "circular shape" and "slightly opaque boundary" representing the findings of the current images 34 and 35 from the input unit 15. The document creation unit 51 creates a new interpretation report on the basis of the newly input character information. For example, the newly input character information is added to the interpretation report of "a nodule of 23×19 mm is recognized in the lower lobe position S6b of the right lung." to create an interpretation report of "a nodule having a circular shape of 23×19 mm with slightly opaque boundaries is recognized in the lower lobe position S6b of the right lung.". The display control unit 23 displays the newly created interpretation report on the display unit 14. It should be noted that in the first embodiment, the interpretation report displayed on the display unit 14 is assumed as the current report.

The visible information reception unit 21 receives the visible information included in the current report. It should be noted that in the first embodiment, "visible information" is assumed as character information, but the present invention is not limited to character information, and includes not only character information included in a current medical document but also image information representing image information and characters. In addition, the "character information" means information formed by characters included in the current medical document. Further, since a character string is a group of characters, the "character string" in the present invention includes a character string composed of one character. Further, "characters" also include a number, a symbol, and the like.

In the first embodiment, the visible information reception unit 21 acquires and receives the sentence of "a nodule having a circular shape of 23×19 mm with slightly opaque boundaries is recognized in the lower lobe position S6b of the right lung." displayed in the creation region 36 of FIG. 3 as character information.

The processing unit 22 performs processing of suppressing a part of the content indicated by the character information received by the visible information reception unit 21 on the basis of at least one of a past image, a past medical document, or a predetermined rule. In the present invention, the "processing of suppressing" is intended to reduce, that is, delete a part of the content indicated by the visible information (including the character information). The suppression processing by the processing unit 22 will be described in detail later.

The display control unit 23 displays the interpretation report creation screen 30 including the current images 34 and 35 and the current report on the display unit 14.

Figure 4:
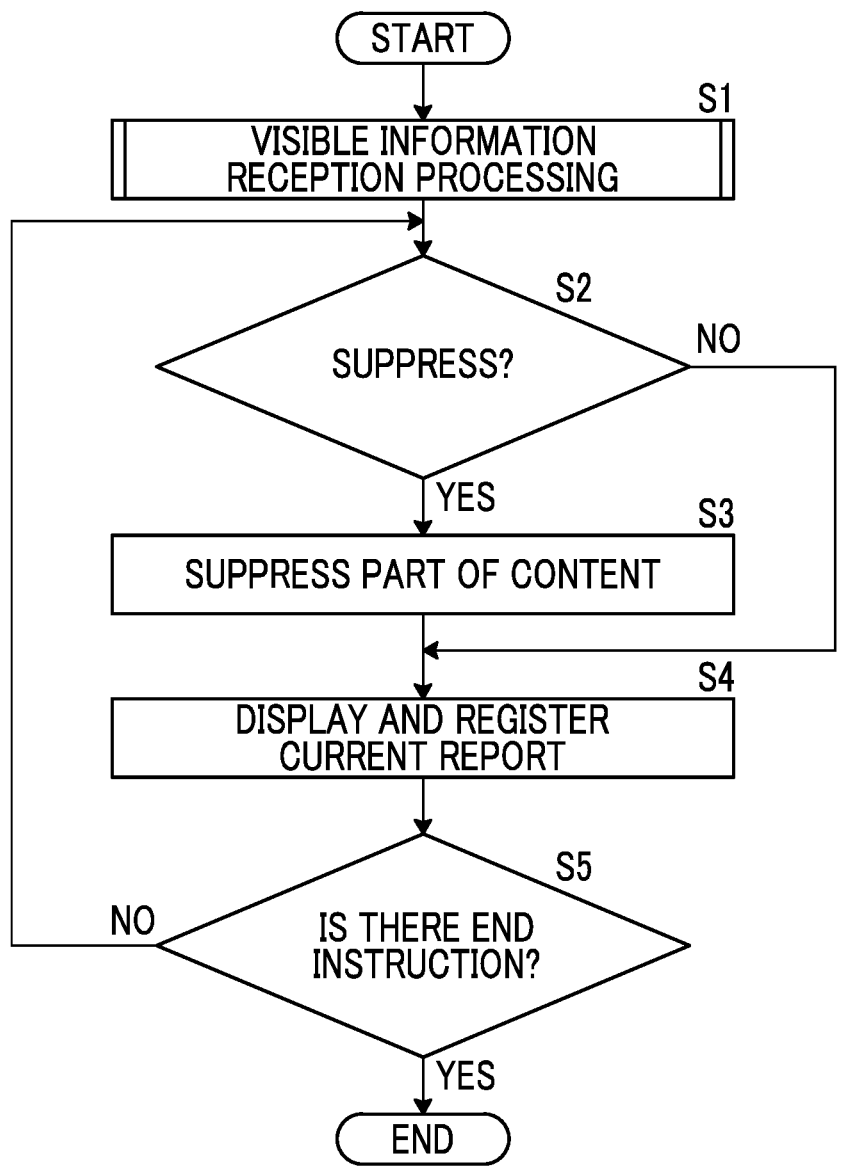
FIG. 4 is a flowchart showing medical document creation support processing performed in the first embodiment of the present invention.
Figure 5:
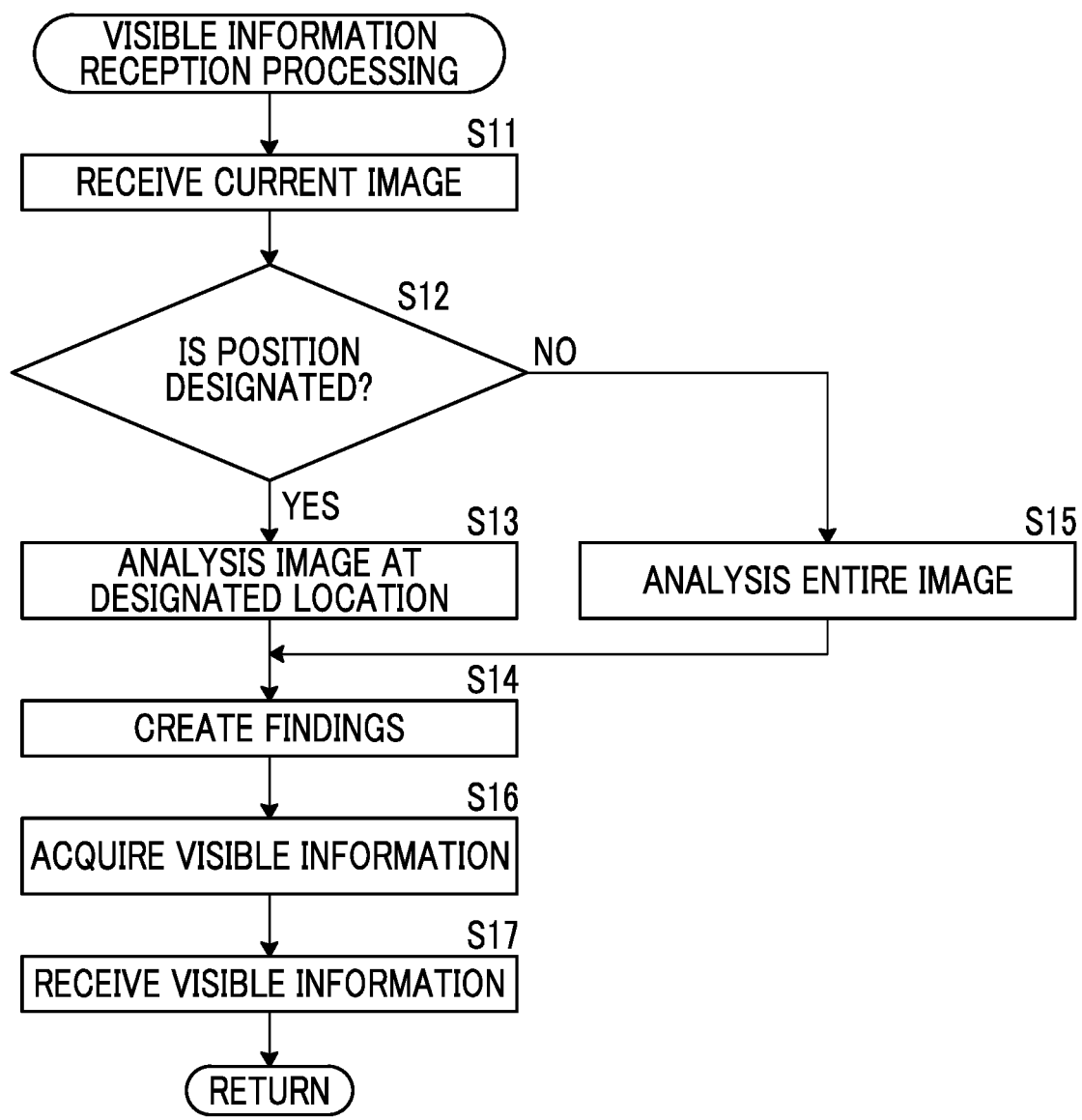
FIG. 5 is a flowchart showing visible information reception processing performed in the first embodiment of the present invention.

Next, the medical document creation support processing performed in the first embodiment will be described. In the first embodiment, as an example, medical document creation support processing at the time of creating an interpretation report for the current image 35 constituting the CT image acquired for one subject will be described. It should be noted that the interpretation report created herein is assumed as a current report. FIG. 4 is a flowchart showing the medical document creation support processing performed in the first embodiment, FIG. 5 is a flowchart showing the visible information reception processing performed in the first embodiment, FIG. 6 is a diagram for explaining a designation of a position and a display of a content of findings in a current image, and FIG. 7 is a diagram for explaining a display in which the content of findings is suppressed.

First, in step S1, the visible information reception unit 21 performs the visible information reception processing. Here, the visible information reception processing by the visible information reception unit 21 will be described. In the first embodiment, as shown in FIG. 5 as an example, first, in step S11, the analysis unit 50 acquires the CT image that is a target of the interpretation report to be created this time by searching the storage 13 according to an instruction from the document creation unit 51, and receives the acquired CT image. It should be noted that in the first embodiment, the CT image corresponds to the current image.

In step S12, the analysis unit 50 discriminates whether or not the position is designated by a radiologist. Specifically, as shown in FIG. 6, as an example, a circle cursor 39 for designating a position by the radiologist is displayed so as to overlap the current image 35 forming the CT image received by the analysis unit 50, and the radiologist moves the circle cursor 39 to a desired position by operating the input unit 15. After moving the cursor 39, the radiologist completes the designation of the position, for example, by left-clicking a mouse as the input unit 15, and the analysis unit 50 receives the designation of the position. In step S12, in a case where the position is designated by a radiologist (step S12; YES), the analysis unit 50 analyzes an image at the designated position, that is, an image of a region within the cursor 39.

It should be noted that in the first embodiment, a circle is used as the cursor 39. However, the invention is not limited thereto. For example, an arrow may be used, or other marks may be used. The size of the cursor 39 is not particularly limited, and can be appropriately set and changed by the operator.

On the other hand, in step S12, in a case where the position is not designated by a radiologist (step S12; NO), that is, in a case where the analysis unit 50 does not receive the designation of the position, the analysis unit 50 performs the image analysis of the entire current image 35.

Next, in step S14, the document creation unit 51 creates, as described above, the findings of the interpretation report on the basis of the character information input on the basis of the analysis result by the analysis unit 50, that is, "a nodule of 23×19 mm is recognized in the lower lobe position S6b of the right lung." and the character information of "circular shape" and "slightly opaque boundary" input from the input unit 15 by the operator. In the first embodiment, as shown in FIG. 6, the findings of "a nodule having a circular shape of 23×19 mm with slightly opaque boundaries is recognized in the lower lobe position S6b of the right lung." is created. The display control unit 23 displays the current report including the created findings on the display unit 14.

Next, in step S16, the visible information reception unit 21 acquires the visible information included in the current report, that is, the character information in the first embodiment. Specifically, the findings created by the document creation unit 51, that is, the sentence of "a nodule having a circular shape of 23×19 mm with slightly opaque boundaries is recognized in the lower lobe position S6b of the right lung." is acquired as visible information (character information). Then, in step S17, the visible information (character information) acquired by the visible information reception unit 21 is received. In this way, the visible information reception processing in the first embodiment is performed.

Returning to FIG. 4, in step S2, the processing unit 22 discriminates whether or not to suppress a part of the content indicated by the character information received by the visible information reception unit 21 on the basis of at least one of predetermined rules.

In the first embodiment, the predetermined rules are determined by whether or not a diagnostician in a place where the current report is submitted prefers a concise description in the current report, that is, the preference of the diagnostician in the place where the current report is submitted. Specifically, in a case where the diagnostician prefers a concise description, the processing of suppressing a part of the content indicated by the character information is performed, and in a case where the diagnostician does not prefer a concise description, the processing of suppressing a part of the content indicated by the character information is not performed. It should be noted that a correspondence table that associates whether or not a concise description is preferred for each diagnostician is stored in the storage 13, and the processing unit 22 refers to the correspondence table stored in the storage 13 to discriminates whether or not to perform the above-described suppression processing. Here, the correspondence table is stored in the storage 13 in the first embodiment, but the present invention is not limited to the correspondence table, and other known techniques may be used as long as it is possible to derive whether or not the diagnostician prefers a concise description.

It should be noted that in the first embodiment, the predetermined rules are determined by the preference of the diagnostician in a place where the current report is submitted, but the present invention is not limited thereto and may be, for example, rules determined by operational rules of a hospital to which the diagnostician in a place where the current report is submitted belongs. Specifically, in a case where the hospital prefers a concise description, the processing of suppressing a part of the content indicated by the character information is performed, and in a case where the hospital does not prefer a concise description, the processing of suppressing a part of the content indicated by the character information is not performed.

In a case where the processing unit 22 discriminates in step S2 that it is not suppressed (step S2; NO), the CPU 11 proceeds to step S4. Then, in step S4, the display control unit 23 causes the display unit 14 to display the content of the current report created by the document creation unit 51 as it is. In addition, the CPU 11 registers the current report created by the document creation unit 51 in the interpretation report database 8 through the interpretation report server 7 in association with an ID for identifying the current image 35.

On the other hand, in step S2, in a case where the processing unit 22 discriminates that it is suppressed (step S2; YES), the CPU 11 proceeds to step S3. Then, in step S3, the processing unit 22 performs processing of suppressing a part of the content indicated by the character information received by the visible information reception unit 21. Specifically, the processing unit 22 discriminates that the character string 40 representing "having a circular shape" and a character string 41 representing "with slightly opaque boundaries" shown in FIG. 6 are an unnecessary character string that has low importance for diagnosis by the diagnostician, and sets the character strings as a non-display. In addition, the processing unit 22 discriminates that character strings other than the character string 40 representing "having a circular shape" and the character string 41 representing "with slightly opaque boundaries" shown in FIG. 6 are a necessary character string that has high importance for diagnosis by the diagnostician, and sets the character strings as a display.

Here, whether or not the character string has low importance for diagnosis by the diagnostician, that is, whether or not the character string is an unnecessary character string can be discriminated by using a discriminator which has been learned to output the probability of whether or not the character string is an unnecessary character string to be input. In the first embodiment, the processing unit 22 includes the discriminator. The discriminator discriminates that the character string is unnecessary in a case where the probability of outputting the character string is equal to or more than a predetermined threshold value.

Next, in step S4, as shown in FIG. 7, the display control unit 23 causes the display unit 14 to display the current report created by the document creation unit 51 by not displaying the character string set to be a non-display by the processing unit 22 in the current report, that is, by suppressing a part of the content indicated by the character information included in the current report. Then, the CPU 11 registers the findings in which a part of the content indicated by the character information included in the current report is suppressed, that is, the current report including the findings displayed in the creation region 36, in the interpretation report database 8 through the interpretation report server 7 in association with the ID for identifying the current image 35.

Then, in step S5, the CPU 11 determines whether or not there is an end instruction in the interpretation WS 3. In a case where there is no end instruction (step S5; NO), the CPU 11 proceeds to step S2 to continue the process from step S2. In a case where there is the end instruction (step S5; YES), the CPU 11 ends a series of processing by the medical document creation support apparatus 10.

As described above, the processing unit 22 performs the processing of suppressing the content indicated by the character information included in the current report on the basis of the predetermined rules. Therefore, the contents unnecessary for diagnosis are suppressed in the current report, so that a diagnostician and a radiologist can easily and quickly grasp the contents necessary for diagnosis described in the medical document.

Next, the interpretation WS 3 including the medical document creation support apparatus according to the second embodiment will be described. It should be noted that in the medical document creation support apparatus of the second embodiment, the description of the same configuration as that of the medical document creation support apparatus of the first embodiment will be omitted, and only a different configuration will be described. FIG. 8 is a diagram for explaining a display in which the content of findings is suppressed in a stepwise manner, and FIG. 9 is another diagram for explaining a display in which the content of findings is suppressed in a stepwise manner.

The processing unit 22 of the second embodiment performs the processing of suppressing the content indicated by the character information included in the current report in a stepwise manner on the basis of the predetermined rules. Specifically, the processing unit 22 comprises a stepwise suppression mode that is turned on and off by the operator operating the input unit 15. It should be noted that as the stepwise suppression mode, for example, three step modes such as a one-step mode, a two-step mode, and a three-step mode can be set. A correspondence table that associates whether or not which step of mode is preferred for each diagnostician or each hospital is stored in the storage 13, and the processing unit 22 refers to the correspondence table stored in the storage 13 to discriminate which step of the suppression processing is to be performed. Here, the correspondence table is stored in the storage 13 in the second embodiment, but the present invention is not limited to the correspondence table, and other known techniques may be used as long as it is possible to derive whether or not how concise is preferred in the description by the diagnostician or the hospital, that is, which step is preferred in the description.

Figure 6:
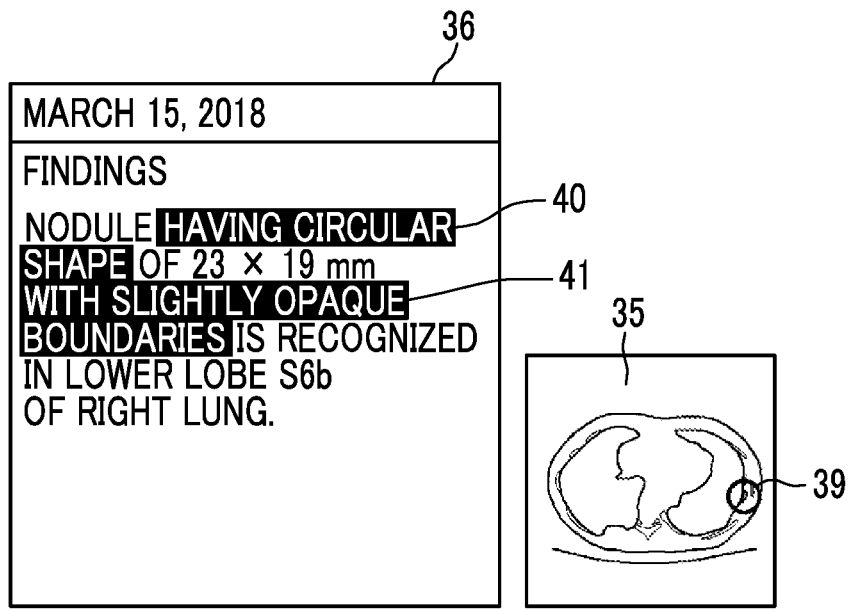
FIG. 6 is a diagram for explaining a designation of a position and a display of a content of findings in a current image.
Figure 7:
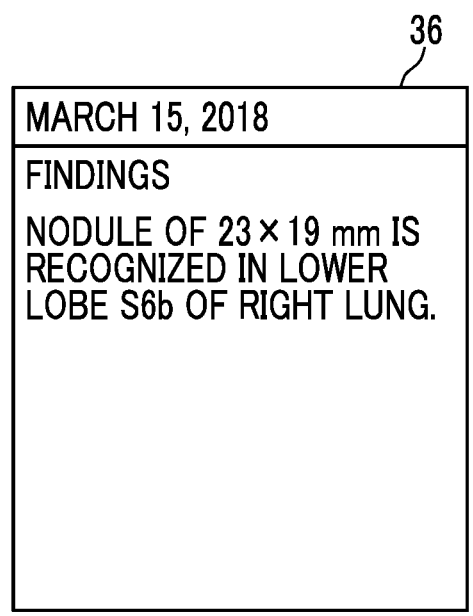
FIG. 7 is a diagram for explaining a display in which a content of findings is suppressed.

Then, in a case where the one-step mode is set, the processing unit 22 sets the character string 41 representing "with slightly opaque boundaries" as a character string having lower importance for diagnosis by the diagnostician, that is, more unnecessary character string, out of the character string 40 representing "having a circular shape" and the character string 41 representing "with slightly opaque boundaries" shown in FIG. 6, to be a non-display. As shown in FIG. 8, the display control unit 23 causes the display unit 14 to display the current report created by the document creation unit 51 by not displaying the character string set to be a non-display by the processing unit 22 in the current report. In addition, the CPU 11 registers the current report including the findings displayed in the creation region 36 of FIG. 8 in the interpretation report database 8 through the interpretation report server 7 in association with an ID for identifying the current image 35.

In a case where the two-step mode is set, the processing unit 22 sets both the character string 40 representing "having a circular shape" and the character string 41 representing "with slightly opaque boundaries" shown in FIG. 6 to be non-displayed as unnecessary character strings. As shown in FIG. 7, the display control unit 23 causes the display unit 14 to display the current report created by the document creation unit 51 by not displaying the character string set to be a non-display by the processing unit 22 in the current report. In addition, the CPU 11 registers the current report including the findings displayed in the creation region 36 of FIG. 7 in the interpretation report database 8 through the interpretation report server 7 in association with an ID for identifying the current image 35.

In a case where the three-step mode is set, the processing unit 22 sets both the character string 40 representing "having a circular shape" and the character string 41 representing "with slightly opaque boundaries" shown in FIG. 6 to be non-displayed as unnecessary character strings. Further, "of 23×19 mm" shown in FIG. 6 is also set to be non-display as an unnecessary character string. In addition, the processing unit 22 also performs processing of converting "a nodule is recognized" shown in FIG. 6 into "a nodule". This processing can be performed by a known technique using, for example, natural language processing.

As shown in FIG. 9, the display control unit 23 does not display the character string set to be a non-display by the processing unit 22 in the current report, and performs processing of converting "a nodule is recognized" into "a nodule" by the processing unit 22, and then the current report created by the document creation unit 51 is displayed on the display unit 14. In addition, the CPU 11 registers the current report including the findings displayed in the creation region 36 of FIG. 7 in the interpretation report database 8 through the interpretation report server 7 in association with an ID for identifying the current image 35.

It should be noted that the discrimination of the character string having lower importance for diagnosis by the diagnostician, that is, that is, more unnecessary character string, can be performed by setting different values of the threshold value in the discriminator included in the processing unit 22. For example, in a case where the probability of outputting the character string is equal to or more than the predetermined first threshold value, it is discriminated that the character string is unnecessary, and in a case where the probability is equal to or more than the second threshold value which is larger than the first threshold value, it is discriminated that the character string is more unnecessary. In addition, in a case where the probability is equal to or more than the third threshold value which is larger than the second threshold value, it is discriminated that the character string is further more unnecessary.

As described above, the preference of the diagnostician or the hospital can be more accurately reflected in the current report by suppressing the content indicated by the character information included in the current report in a stepwise manner, so that the diagnostician and the radiologist can easily grasp the content necessary for the diagnosis described in the current report.

In the second embodiment, one of the three step modes is set for each diagnostician or each hospital, but the present invention is not limited to thereto. For example, whether or not to perform the processing of suppressing a part of the content indicated by the character information is set for each diagnostician or each hospital, and in a case where the current report is submitted to a diagnostician or hospital which is set to perform the processing of suppressing, the processing unit 22 may perform processing of suppressing the content indicated by the character information in the order of the one-step mode, the two-step mode, and the three-step mode each time an operator inputs an input signal from the input unit 15.

Next, the interpretation WS 3 including the medical document creation support apparatus according to the third embodiment will be described. It should be noted that in the medical document creation support apparatus of the third embodiment, the description of the same configuration as that of the medical document creation support apparatus of the first embodiment will be omitted, and only a different configuration will be described.

The processing unit 22 of the third embodiment performs processing of setting a display or a non-display for each item indicated by the character information in the current report. FIG. 10 is a diagram for explaining a display in a case where there are a plurality of items. Here, in the present invention, the "item" means the content of findings created for each position or region designated on the current image. In the third embodiment, the analysis unit 50 performs the image analysis in the entire region of the current image 35, and the document creation unit 51 creates findings for a plurality of parts on the basis of the analysis result by the analysis unit 50.

As shown in FIG. 10, findings 36A, 36B, and 36C respectively corresponding to the three cursors 39A, 39B, and 39C displayed on the current image 35 are displayed on the interpretation report creation screen 30 shown in FIG. 3. The findings 36A, 36B, and 36C are the findings 36A, 36B, and 36C created by the document creation unit 51 for each of the cursors 39A, 39B, and 39C. The processing unit 22 compares each region indicated by the three cursors 39A, 39B, and 39C on a current image 35 with each region respectively corresponding to the three cursors 39A, 39B, and 39C on the current image 35 in the past image acquired for a subject in the current image in the past, and in a case where a change is not observed in the image, sets findings corresponding to a cursor that has not changed to a non-display.

It should be noted that the current image 35 and the past image are compared in the third embodiment, but the present invention is not limited to thereto. The findings 36A, 36B, and 36C created for each region respectively corresponding to the three cursors 39A, 39B, and 39C on the current image 35 may be compared with the findings created for each region respectively corresponding to the three cursors 39A, 39B, and 39C on the current image 35 in the past image acquired for a subject in the current image in the past, and findings corresponding to a cursor in which the lesion is not changed may be set to a non-display.

Next, the interpretation WS 3 including the medical document creation support apparatus according to the fourth embodiment will be described. It should be noted that in the medical document creation support apparatus of the fourth embodiment, the description of the same configuration as that of the medical document creation support apparatus of the first embodiment will be omitted, and only a different configuration will be described.

The processing unit 22 of the fourth embodiment performs processing of combining the contents indicated by two or more items in a case where there are a plurality of items indicated by the character information in the current report. As shown in FIG. 10, in a case where the findings 36A, 36B, and 36C respectively corresponding to the three cursors 39A, 39B, and 39C on the current image 35 are displayed, the finding 36A is assumed as a finding content shown in FIG. 6, the finding 36B is assumed as a finding content of "no change in the lower lobe S5 of the left lung.", and the finding 36C is assumed as a finding content of "no change in the lower lobe S1 of the left lung.".

Figure 11:
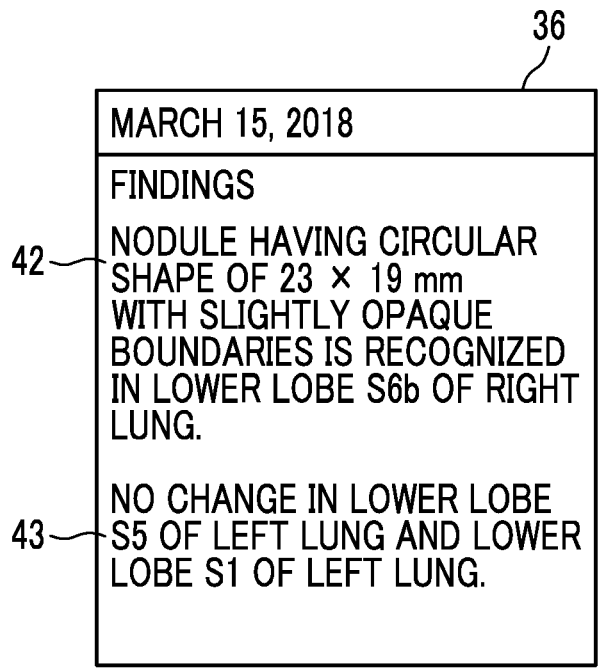
FIG. 11 is a diagram for explaining a display in which two or more items are combined.

In this case, the processing unit 22 performs processing of combining the finding 36A, the finding 36B, and the finding 36C. FIG. 11 is a diagram for explaining a display in which two or more items are combined. Specifically, as shown in FIG. 11, a finding content 42 of the finding 36A is left as it is, and the finding contents of the finding 36B and the finding 36C are combined to form a finding content 43 of "no change in the lower lobe S5 of the left lung and the lower lobe S1 of the left lung.".

As described above, in a case where there are the three findings, the processing unit 22 performs the processing of combining the three findings into one finding to suppress the finding content, that is, the content indicated by the character information, so that the display control unit 23 can display the finding whose content is suppressed in the creation region 36 as shown in FIG. 11. As a result, the diagnostician and the radiologist can view the current report that has been concisely summarized, and can easily and quickly grasp the contents necessary for diagnosis.

Next, the interpretation WS 3 including the medical document creation support apparatus according to the fifth embodiment will be described. It should be noted that in the medical document creation support apparatus of the fifth embodiment, the description of the same configuration as that of the medical document creation support apparatus of the first embodiment will be omitted, and only a different configuration will be described.

Similar to the fourth embodiment, the processing unit 22 of the fifth embodiment performs processing of combining the contents indicated by two or more items in a case where there are a plurality of items indicated by the character information in the current report. Further, similar to the second embodiment, the processing unit 22 performs the processing of suppressing the content indicated by the character information included in the current report in a stepwise manner on the basis of a predetermined rule.

Figure 12:
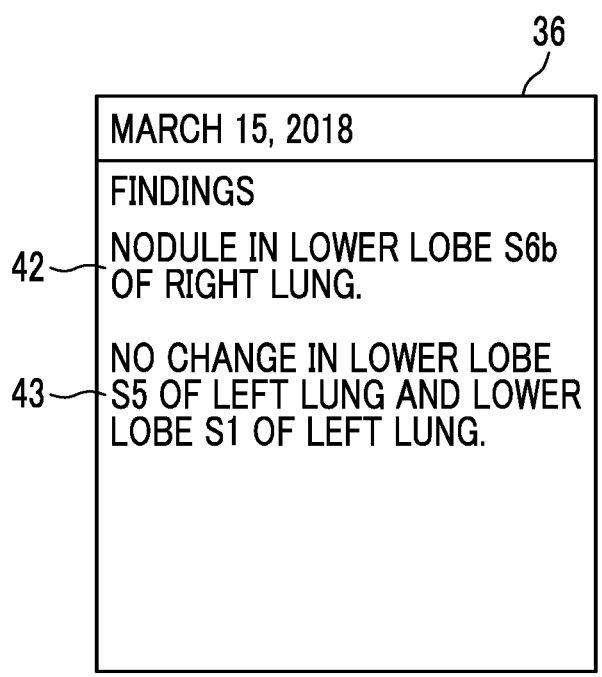
FIG. 12 is a diagram for explaining a display in which two or more items are combined and a content of findings is suppressed.

FIG. 12 is a diagram for explaining a display in which two or more items are combined and a content of findings is suppressed. Specifically, the processing unit 22 further performs the three-step mode suppression processing performed in the second embodiment on the finding content 42 shown in FIG. 11 to perform processing of suppressing the finding content of "a nodule having a circular shape of 23×19 mm with slightly opaque boundaries is recognized in the lower lobe position S6b of the right lung." to a finding content of "a nodule in the lower lobe position S6b of the right lung." as shown in FIG. 12.

It should be noted that in the fifth embodiment, the processing unit 22 performs the three-step mode suppression processing, but the present invention is not limited thereto, and the processing unit 22 may perform the one-step mode and the two-step mode suppression processing. In addition, the processing unit 22 may perform the same suppression processing as in the first embodiment.

As described above, in a case where there are the three findings, the processing unit 22 performs the processing of combining the three findings into one finding, and performs processing of suppressing the contents indicated by the character information included in the current report in a stepwise manner on the basis of a predetermined rule, so that the finding content, that is, the content indicated by the character information, can be made more concise.

Figure 13:
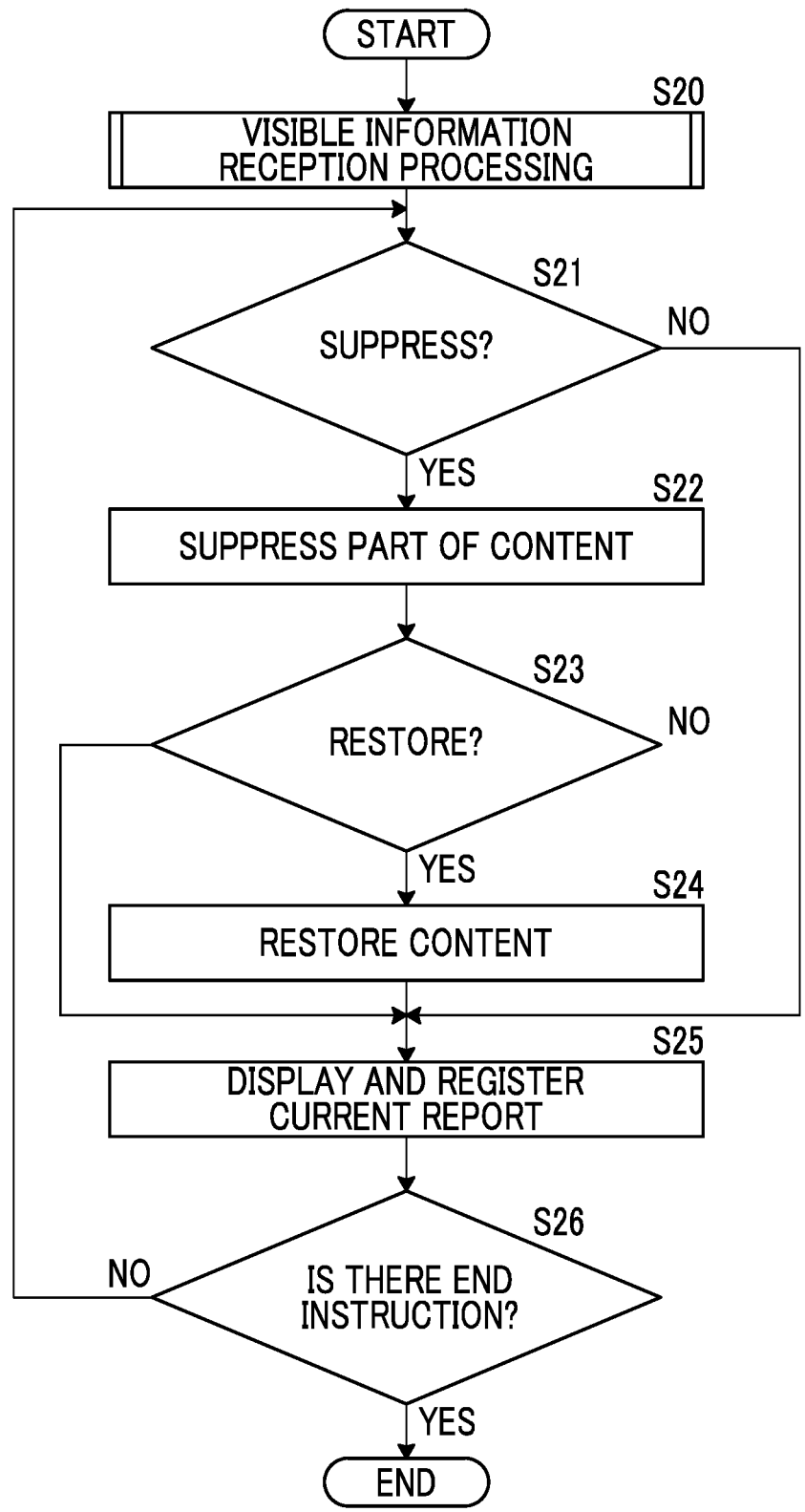
FIG. 13 is a flowchart showing medical document creation support processing performed in the sixth embodiment.

Next, the interpretation WS 3 including the medical document creation support apparatus according to the sixth embodiment will be described. It should be noted that in the medical document creation support apparatus of the sixth embodiment, the description of the same configuration as that of the medical document creation support apparatus of the first embodiment will be omitted, and only a different configuration will be described. The processing unit 22 of the sixth embodiment is different from that of the first embodiment in that the processing unit 22 has a full display mode that is a mode for restoring the suppressed contents. FIG. 13 is a flowchart showing medical document creation support processing performed in the sixth embodiment.

First, in step S20, the visible information reception unit 21 performs the visible information reception processing. It should be noted that step S20 is the same processing as step S1 in FIG. 4, and description thereof will be omitted here.

In step S21, the processing unit 22 discriminates whether or not to suppress a part of the content indicated by the character information received by the visible information reception unit 21 on the basis of at least one of the past image, the past report, or a predetermined rule.

In a case where the processing unit 22 discriminates in step S21 that it is not suppressed (step S21; NO), the CPU 11 proceeds to step S25. Then, in step S25, the display control unit 23 causes the display unit 14 to display the content of the current report created by the document creation unit 51 as it is. In addition, the CPU 11 registers the current report created by the document creation unit 51 in the interpretation report database 8 through the interpretation report server 7 in association with an ID for identifying the current image 35.

On the other hand, in step S21, in a case where the processing unit 22 discriminates that it is suppressed (step S21; YES), the CPU 11 proceeds to step S22. Then, in step S22, the processing unit 22 performs processing of suppressing a part of the content indicated by the character information received by the visible information reception unit 21. It should be noted that the suppression processing performed by the processing unit 22 is the same as the processing described in the above-described embodiment, and thus the detailed description thereof is omitted here.

Next, in step S23, the processing unit 22 discriminates whether or not to restore the contents suppressed in step S22. In the sixth embodiment, the processing unit 22 has the full display mode as a mode for restoring the contents suppressed in step S22. The full display mode can be turned on and off by an operator operating the input unit 15.

In a case where the processing unit 22 discriminates in step S23 that the content is restored, that is, in a case where the processing unit 22 discriminates that the full display mode is turned on (step S23; YES), the processing unit 22 performs processing of restoring the content suppressed in step S22 to the content before suppression in step S24, for example, as shown in FIG. 6. Then, next, in step S25, the display control unit 23 causes the display unit 14 to display the content of the current report including the content of the finding shown in FIG. 6, that is, the content of the current report created by the document creation unit 51. In addition, the CPU 11 registers the current report created by the document creation unit 51 in the interpretation report database 8 through the interpretation report server 7 in association with an ID for identifying the current image 35.

On the other hand, in a case where the processing unit 22 discriminates in step S23 that the content is not restored, that is, in a case where the processing unit 22 discriminates that the full display mode is turned off (step S23; NO), the display control unit 23 causes the display unit 14 to display a current report in which a part of the content indicated by the character information is suppressed. Then, the CPU 11 registers the findings in which a part of the content indicated by the character information included in the current report is suppressed, that is, the current report including the findings displayed in the creation region 36, in the interpretation report database 8 through the interpretation report server 7 in association with the ID for identifying the current image 35.

Then, in step S26, the CPU 11 determines whether or not there is an end instruction in the interpretation WS 3. In a case where there is no end instruction (step S26; NO), the CPU 11 proceeds to step S21 to continue the process from step S21. In a case where there is the end instruction (step S26; YES), the CPU 11 ends a series of processing by the medical document creation support apparatus 10.

According to the above, for example, in a case where the content indicated by the character information received by the visible information reception unit 21 is excessively suppressed by the processing unit 22, that is, excessively deleted and the content of the current report is difficult to understand, an original content can be confirmed, so that the radiologist and the diagnostician can surely grasp the content of the current report.

It should be noted that in the sixth embodiment, in a case where the full display mode is turned on, the processing unit 22 performs the processing of restoring all the suppressed contents, but the present invention is not limited to thereto. The content indicated by the character information included in the current report may be restored in a stepwise manner. Specifically, the processing unit 22 performs the processing of restoring the contents indicated by the character information in the order of the three-step mode, the two-step mode, and the one-step mode described in the second embodiment.

In addition, in the above-described embodiment, the current image is a tomographic image forming a three-dimensional image that is a CT image, but the present invention is not limited thereto. The three-dimensional image may be an MRI image, and the current image may be a tomographic image forming a three-dimensional image that is an MRI image.

In addition, in the above-described embodiment, the present invention is applied to the case of creating an interpretation report as a current medical document, but the present invention can also be applied to the case of creating medical documents other than the interpretation report such as an electronic medical record and a diagnosis report.

In addition, in the above-described embodiment, the analysis unit 50 that analyzes the medical image is provided in the interpretation WS 3, but the present invention is not limited to thereto. In the interpretation WS 3, analysis results analyzed by an external analysis apparatus may be acquired, and the acquired analysis results may be used to create the current medical document.

In addition, in the above-described embodiment, the document creation unit 51 that creates a current medical document is provided in the interpretation WS 3, but the present invention is not limited to thereto. In the interpretation WS 3, a current medical document created by an external document creation apparatus or a current medical document created by at least one of a radiologist or a diagnostician is acquired and the acquired current medical document may be used. For example, a current medical document in which the diagnostician additionally writes a character string may be used for a current medical document created by the radiologist.

In addition, in the above-described embodiment, the current medical document is a document on the basis of the current image obtained by imaging a subject, but the present invention is not limited to thereto. For example, a current medical document that is not created while viewing the current image, that is, a current medical document that is not on the basis of the current image may be used. For example, a medical certificate created by a diagnostician who examines a patient in front of the diagnostician can be used as a current medical document. In addition, the current medical document may be a document created by copying a sentence automatically created on the basis of the analysis result of the past image of the subject and/or the past report.

In addition, in the above-described embodiment, the past image and the past medical document are the information acquired in the past for the subject in the current image, but the present invention is not limited to thereto. The past image and the past medical document may be information targeting a subject different from a subject who is a target of the current medical document. Specifically, the processing unit 22 refers to the analysis result of the current image 35, and requests the interpretation report server 7 to provide an interpretation report (correspond to a past medical document) of a similar case similar to the case included in the current image 35. The interpretation report server 7 refers to the interpretation report database 8 and transmits the requested interpretation report to the interpretation WS 3. It should be noted that at a point in time at which the analysis result of the current image 35 of the patient is acquired, the processing unit 22 may request the interpretation report server 7 to acquire the past interpretation report, and store the acquired interpretation report in the storage 13. It should be noted that in a case of extracting the past medical document, a method generally used in the field of artificial intelligence, that is, AI, such as machine learning, can be used.

In addition, the processing unit 22 refers to the analysis result of the current image 35, and requests the image server 5 to provide a past image of a similar case similar to the case included in the current image 35. The image server 5 refers to the image database 6 and transmits the requested image data to the interpretation WS 3. The image data of the past image transmitted to the interpretation WS 3 is stored in the storage 13. It should be noted that at the point in time at which the analysis result of the current image 35 of the patient is acquired, the processing unit 22 may request the image server 5 to acquire the past image data, and may store the acquired image data in the storage 13. It should be noted that in a case of extracting the past image, a method generally used in the field of artificial intelligence, that is, AI, such as machine learning, can be used. In addition, in a case of searching for the image, a generally used similarity search method may be used.

As described above, in a case where the past image and the past medical document are information targeting a subject different from a subject who is a target of the current medical document, the processing unit 22 performs processing of setting a character string having low importance for diagnosis by a diagnostician to a non-display on the basis of information such as diagnosis, progress information, lesion name, lesion position information, and findings about another subject described in the past medical document created for the acquired past image and/or the acquired past medical document. It should be noted that whether or not the importance of the character string is low can be discriminated by using a discriminator which has been learned to output a probability that the importance of the character string inputted for diagnosis by the diagnostician is low in a case where the character string is inputted. The processing unit 22 has this discriminator. The discriminator discriminates that the character string has low importance in a case where the probability of outputting the character string is equal to or more than a predetermined threshold value. It should be noted that the degree of importance can be discriminated in a stepwise manner by setting a plurality of threshold values. As a result, the processing unit 22 can set only the character strings having lower importance to a non-display.

In addition, in the above-described embodiment, the processing unit 22 performs control to suppress a part of the content indicated by the visible information received by the visible information reception unit 21, but the present invention is not limited thereto, and the processing unit 22 may perform processing of suppressing at least a part of the content indicated by the visible information.

The disclosure of JP2018-072523 filed on Apr. 4, 2018 is herein incorporated by reference in its entirety in this application.

All publications, patent applications, and technical standards described in this application are herein incorporated by reference in this application as the case in which each of publication, patent application, and technical standard is specifically and individually described to be incorporated by reference.

What is claimed is:

1. A medical document creation support apparatus comprising:
   a processor, configured to:
   receive visible information included in a current medical document, wherein the visible information is character information;
   perform learning of a discriminator which is a learned model by using a plurality of character strings as inputs and using probabilities of importance of the respective character strings for diagnosis as outputs; and
   perform processing of suppressing a part of a content indicated by the visible information on the basis of at least one of a past image, a past medical document, or a predetermined rule,
   wherein the processor discriminates, by setting a plurality of threshold values, a degree of importance of each character string indicated by the character information in the current medical document in a stepwise manner by using the discriminator which has been learned to output a probability of outputting each character string, and sets a display or a non-display for each character string in accordance with the degree of importance.

2. The medical document creation support apparatus according to claim 1,
   wherein the processor performs processing of setting a display or a non-display for each item indicated by the visible information in the current medical document.

3. The medical document creation support apparatus according to claim 1,
   wherein in a case where there are a plurality of items indicated by the visible information, the processor performs processing of combining contents indicated by two or more items in the current medical document.

4. The medical document creation support apparatus according to claim 1,
   wherein the processor performs processing of restoring a content indicated by the suppressed visible information.

5. The medical document creation support apparatus according to claim 1,
   wherein the processor performs processing of suppressing the content indicated by the visible information in a stepwise manner.

6. The medical document creation support apparatus according to claim 1,
   wherein the processor performs processing of restoring the content indicated by the suppressed visible information in a stepwise manner.

7. The medical document creation support apparatus according to claim 1,
   wherein the past image and the past medical document are information targeting a subject different from a subject who is a target of the current medical document.

8. The medical document creation support apparatus according to claim 1,
   wherein the current medical document is a document based on a current image obtained by imaging a subject.

9. The medical document creation support apparatus according to claim 8,
   wherein the processor receives visible information based on a current medical document created on the basis of an image analysis result of a position designated on the current image.

10. The medical document creation support apparatus according to claim 8,
    wherein the processor receives visible information based on a current medical document created on the basis of an image analysis result of the entire current image.

11. The medical document creation support apparatus according to claim 8,
    wherein the processor receives visible information based on a current medical document created on the basis of a past image or a past medical document acquired in the past for a subject in the current image.

12. The medical document creation support apparatus according to claim 8,
    wherein the processor receives visible information based on a current medical document created by at least one of a radiologist or a diagnostician on the basis of the current image.

13. The medical document creation support apparatus according to claim 1, wherein
    the processor performs processing of setting the display or the non-display for each character string indicated by the character information in the current medical document in an order of a first mode, a second mode, and a third mode each time an input signal is input by an input apparatus by using the discriminator,
    in a case where the probability of outputting the character string output by the discriminator is equal to or more than a first threshold value, the character string is set to be the non-display in the first mode,
    in a case where the probability of outputting the character string output by the discriminator is equal to or more than a second threshold value which is larger than the first threshold value, the character string is set to be the non-display in the second mode, and
    in a case where the probability of outputting the character string output by the discriminator is equal to or more than a third threshold value which is larger than the second threshold value, the character string is set to be the non-display in the third mode.

14. A medical document creation support method comprising:
    receiving visible information included in a current medical document based on a current image acquired by imaging a subject, wherein the visible information is character information;
    perform learning of a discriminator which is a learned model by using a plurality of character strings as inputs and using probabilities of importance of the respective character strings for diagnosis as outputs; and
    performing processing of suppressing a content indicated by the received visible information on the basis of at least one of a past image, a past medical document, or a predetermined rule,
    wherein a degree of importance of each character string indicated by the character information in the current medical document is discriminated in a stepwise manner by setting a plurality of threshold values by using discriminator which has been learned to output a probability of outputting each character string, and a display or a non-display is set for each character string in accordance with the degree of importance.

15. A non-transitory computer-readable storage medium storing therein a medical document creation support program for causing a computer to execute:
- a procedure for receiving visible information included in a current medical document based on a current image acquired by imaging a subject, wherein the visible information is character information;
- a procedure for performing learning of a discriminator which is a learned model by using a plurality of character strings as inputs and using probabilities of importance of the respective character strings for diagnosis as outputs; and
- a procedure for performing processing of suppressing a content indicated by the received visible information on the basis of at least one of a past image, a past medical document, or a predetermined rule,
- wherein a degree of importance of each character string indicated by the character information in the current medical document is discriminated in a stepwise manner by setting a plurality of threshold values by using the discriminator which has been learned to output a probability of outputting each character string, and a display or a non-display is set for each character string in accordance with the degree of importance.

* * * * *